United States Patent [19]

Vora et al.

[11] Patent Number: 4,754,078

[45] Date of Patent: Jun. 28, 1988

[54] INTEGRATED ETHERIFICATION PROCESS WITH ISOMERIZATION PRETREATMENT

[75] Inventors: Bipin V. Vora, Darien; Peter R. Pujado, Palatine; Richard E. Conser, Golf, all of Ill.

[73] Assignee: UOP Inc., Des Plaines, Ill.

[21] Appl. No.: 20,806

[22] Filed: Mar. 2, 1987

[51] Int. Cl.$^4$ .............................................. C07C 41/06
[52] U.S. Cl. ..................................... 568/697; 585/331
[58] Field of Search ......................... 568/697; 585/331

[56] References Cited

U.S. PATENT DOCUMENTS

| | | | |
|---|---|---|---|
| 2,720,547 | 10/1955 | Wolff et al. | 260/614 |
| 3,726,942 | 4/1973 | Louder | 260/683.61 |
| 4,118,425 | 10/1978 | Herbstman | 260/614 |
| 4,219,678 | 8/1980 | Obenaus et al. | 568/697 |
| 4,252,541 | 2/1981 | Herbstman | 44/56 |
| 4,329,516 | 5/1982 | Al-Muddarris | 568/697 |

OTHER PUBLICATIONS

Chemical Engineering News, Jun. 25, 1979 Edition, p. 35.
Paper presented at the American Institute of Chemical Engineers 85th National Meeting on Jun. 4–8, 1978 by F. Obenaus et al.

*Primary Examiner*—Howard T. Mars
*Attorney, Agent, or Firm*—Thomas K. McBride; John F. Spears, Jr.; John G. Tolomei

[57] ABSTRACT

A multistep hydrocarbon conversion process for the production of ethers including methyl tertiary butyl ether (MTBE) from light paraffins and alcohols is disclosed. A mixture of $C_4$ isoparaffins, normal paraffins, an etherification recycle and butane isomerization effluent enter a deisobutanizer column. Normal paraffins withdrawn from the fractionator are isomerized and returned to the fractionator, and isoparaffins are withdrawn from the fractionator and dehydrogenated. The resulting olefins enter an etherification zone for reaction of isobutene with a $C_2$–$C_5$ alcohol. Unreacted paraffins and olefins comprise the etherification effluent entering the deisobutanizer. Normal butanes and olefins are withdrawn as a sidecut from the deisobutanizer. Hydrogenation of the sidecut saturates any olefins contained therein which would interfere with the isomerization of normal butanes. The saturated sidecut passes to an isomerization zone and a mixture of isobutane and normal butane is recycled to the deisobutanizer. In a highly perferred embodiment, spent catalyst from the isomerization zone fulfills the catalyst requirement of the dehyrogenation zone.

11 Claims, 1 Drawing Sheet

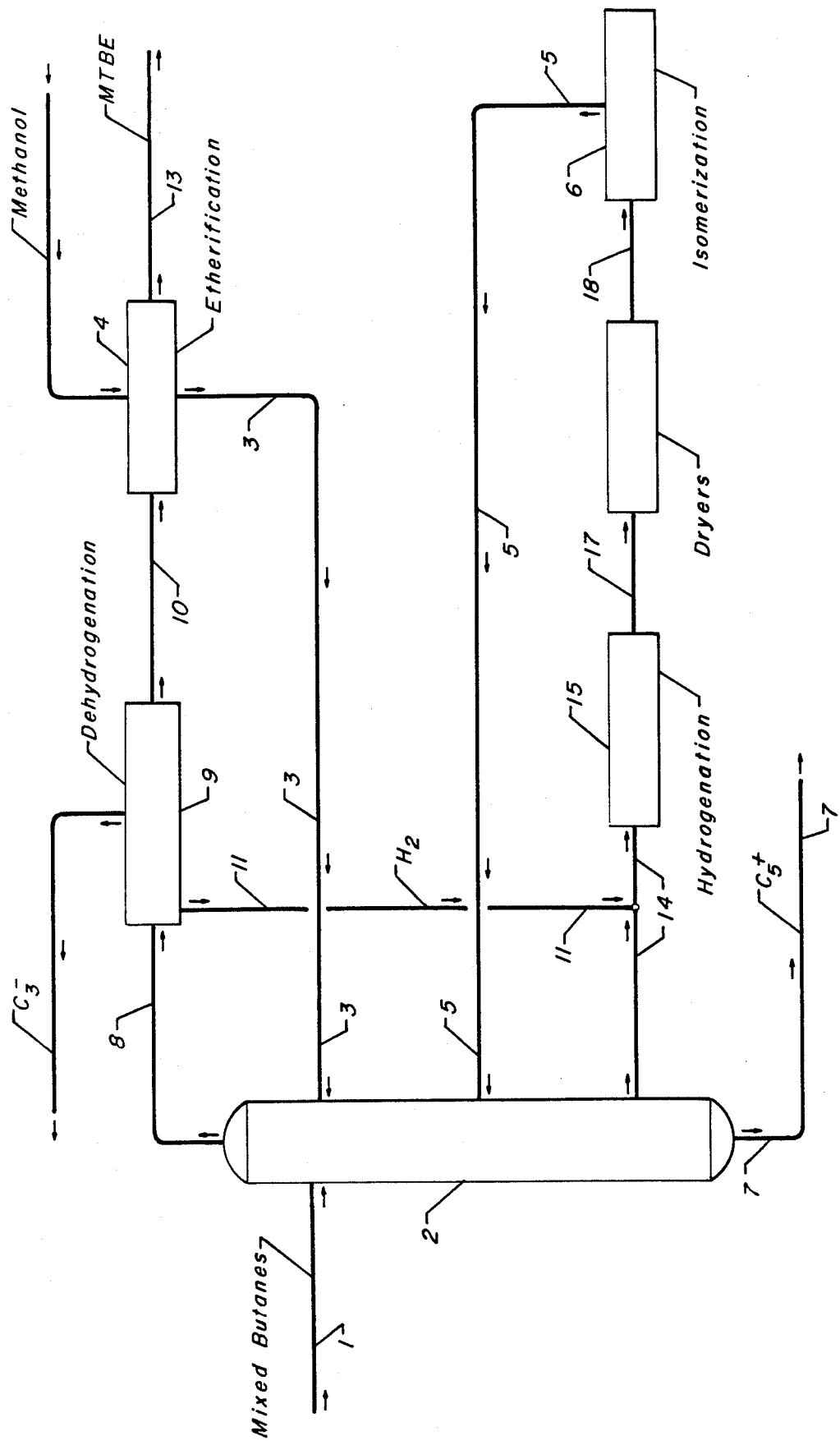

४,७५४,०७८

INTEGRATED ETHERIFICATION PROCESS WITH ISOMERIZATION PRETREATMENT

BACKGROUND OF THE INVENTION

1. Field of the Invention

The invention relates to multistep hydrocarbon conversion processes which produce ethers from an alcohol feed stream and a feed stream comprising light paraffins. The invention more directly relates to integrated processes which utilize paraffin isomerization and paraffin dehydrogenation steps to produce isoolefins for subsequent reaction with an alcohol in an etherification zone. The invention is specifically related to the circulation of olefin containing streams between the dehydrogenation and the isomerization zone.

2. Prior Art

Etherification processes are utilized to produce large amounts of gasoline boiling range ethers for use as antiknock compounds in lead-free gasoline. Ethers may also be produced as a means of making pure isoolefins. For instance, plans have been announced to produce pure isobutene for the manufacture of polyisobutylenes and tert-butyl-phenol by cracking methyl tertiary butyl ether (MTBE), with the methanol being recycled. The predominant etherification process involves the reaction of an alcohol with an isoolefin, with $C_4$ and $C_5$ isoolefins being the preferred feedstock. As the supply of $C_4$ and $C_5$ isoolefins is rather limited since they are mainly produced as by-products of fluidized catalytic cracking or steam cracking, it is often necessary to produce the isoolefins by the sequential steps of isomerization and dehydrogenation.

The production of ethers by the reaction of an isoolefin with an alcohol is well known and is practiced commercially. This highly selective reaction is also used to remove isoolefins, especially isobutylene, from mixed hydrocarbon streams such as the $C_4$ streams produced in steam cracking plants which produce ethylene. Increased attention has been focused on ether production due to the rapidly increasing demand for lead-free octane boosters for gasoline such as MTBE. A detailed description of processes, including catalysts, processing conditions and product recovery, for the production of MTBE from isobutylene and methanol are provided in U.S. Pat. Nos. 2,720,547 and 4,219,678 and in an article at page 35 of the June 25, 1979 edition of *Chemical and Engineering News*. The preferred process is described in a paper presented at the American Institute of Chemical Engineers 85th National Meeting on June 4-8, 1978 by F. Obenaus, et al. Descriptions of integrated processes, including those which utilize butane isomerization and/or butane dehydrogenation, are found in U.S. Pat. Nos. 3,726,942, 4,118,425, 4,252,541 and 4,329,516.

Except for U.S. Pat. No. 3,726,942, all of the process arrangements include an isomerization step ahead of and isolated from a dehydrogenation and further processing steps. Since the isomerization of relatively short chain paraffins yields a fixed ratio of isoparaffin to paraffin, it is advantageous to recycle unconverted paraffins back to the isomerization reactor. Recycling of unconverted normal paraffins has usually been performed by separating the normal paraffins from the effluent of the isomerization reactor.

The above schemes suffer two drawbacks. First, the feed to the isomerization process must consist essentially of normal paraffins and isoparaffins. This makes the process adaptable only to such feeds or requires additional processing facilities to remove other components. In addition, process streams containing unbranched paraffins that originate downstream of the isomerization zone cannot be recycled to the isomerization zone without first having the non-paraffinic components removed. This again adds cost and complexity to the overall etherification process by requiring additional processing facilities.

SUMMARY OF THE INVENTION

It is a broad object of this invention to produce ethers, such as MTBE from mixed paraffins and olefins, and a $C_1$–$C_5$ alcohol.

Another object of this invention is to reduce the number of intermediate separations that are needed to produce ethers from alcohol and mixed paraffins and olefins.

A yet further object of this invention is to maximize ether production from olefins, paraffins and alcohol by providing facilities for recycling unbranched paraffins and olefins to an isomerization zone.

It is a more specific objective of this invention to provide an improved process for producing ethers from an alcohol and a hydrocarbon feed stream comprising saturate normal $C_4$-plus hydrocarbons which are converted to isoolefins by isomerization and dehydrogenation.

It is a general objective of the invention to reduce the capital costs in an integrated process for producing ethers.

It is a still further objective of the invention to provide an integrated process for producing methyl tertiary butyl ether.

The invention provides an integrated multistep process for the production of methyl tertiary butyl ether and other ethers from precursor light paraffins, olefins and alcohols. In simplest form a feed stream enters a fractionation column along with a recycle stream from an etherification zone. The column supplies an overhead stream containing primarily isoparaffins which enter a dehydrogenation zone. Effluent from the dehydrogenation zone is separated to remove lighter hydrocarbons before the remainder of the stream enters an etherification zone. Alcohol charged to the etherification zone reacts with the isoolefins to form an ether which is removed from the process as the primary product. The effluent from the etherification zone which is not withdrawn as product is recycled, after removal of oxygenates, to the fractionation column. Below the point of etherification zone recycle, a sidecut consisting primarily of normal paraffins is removed from the fractionation column. This sidecut stream may also contain mono- or diolefins that either entered with the feed or were recycled to the column from the etherification zone. The sidecut stream first undergoes hydrogenation to saturate any olefins present therein. Hydrogenation serves to remove olefins that would otherwise interfere with the isomerization zone by increasing the rate of carbon deposition on the isomerization catalyst and, therefore, incrementing the rate of deactivation of the catalyst. Paraffins from the hydrogenated sidecut stream then enter an isomerization zone to at least partially convert paraffins into isoparaffins. The isoparaffin enriched sidecut stream is then returned to the fractionation column wherein the isoparaffins are drawn toward the overhead stream and remaining normal paraffins can be drawn off again into the sidecut stream.

In this manner the process of this invention combines the necessary dehydrogenation and isomerization zones for maximizing the available isoolefin precursor for an etherification zone in a process arrangement that reduces the amount of separation facilities.

One embodiment of this invention may be broadly characterized as a hydrocarbon conversion process which comprises the steps of passing a feed stream of $C_4$-$C_6$ paraffins to a fractionation section; recovering a stream which is rich in isoparaffin from the fractionation section; passing the isoparaffin rich stream to a dehydrogenation unit and recovering a first effluent stream which is rich in the isoolefin corresponding to the isoparaffin in the isoparaffin rich stream; passing at least a portion of the isoolefin from the first effluent stream and a $C_1$-$C_5$ alcohol to an etherification zone and recovering a second effluent stream; separating the second effluent stream to recover an ether rich product stream and a hydrocarbonaceous first recycle stream; returning the recycle stream to the fractionation column; recovering a higher boiling stream from the fractionation section, comprising normal paraffins and containing olefins; passing the higher boiling stream to a hydrogenation zone to saturate the olefins and recovering a saturated hydrocarbon stream; passing the saturated hydrocarbon stream to an isomerization zone and recovering a third effluent stream containing corresponding isoparaffins and normal paraffins; and returning the third effluent stream to the fractionation column.

In a highly preferred form of this invention the isomerization zone uses a platinum type catalyst. This catalyst, after a period of use, will lose its isomerization function; however, it will retain a hydrogenation function. As a result, operating costs for the process are reduced by running the hydrogenation zone with used catalysts from the isomerization zone. However, other common hydrogenation catalysts containing palladium or nickel may be used, if desired.

BRIEF DESCRIPTION OF THE DRAWING

The drawing is a schematic representation of a process in accordance with the above invention for producing methyl tertiary butyl ether from feed streams of mixed butanes and methanol. A feed stream of mixed butanes which is primarily isobutane and normal butane enters the fractionation column through line 1. The fractionation column 2 is a deisobutanizer column which also receives, via line 3, a recycle stream containing isobutane from etherification zone 4, together with smaller amounts of propane, isobutene, normal butene, butadiene, and normal butane from etherification zone 4 and, through recycle line 5, a mixture of normal butane and isobutane from isomerization zone 6. The deisobutanizer column 2 rejects any $C_5$ or higher hydrocarbons that are present with the feed or formed in trace amounts through a bottoms line 7.

An overhead stream 8 which is rich in isobutane passes from the deisobutanizer 2 to a dehydrogenation zone 9. When used herein the term rich is defined to mean a process stream containing at least 55 mole percent of the material described thereby. In the dehydrogenation zone, isobutane is contacted with a dehydrogenation catalyst at butane dehydrogenation conditions. As a result, a dehydrogenation zone effluent comprising isobutane and isobutylene is formed. Separation facilities within the dehydrogenation zone remove hydrogen and $C_1$-$C_3$ hydrocarbons from the dehydrogenation effluent before it is passed, via line 10, to etherification zone 4. At least a portion of the net hydrogen produced by dehydrogenation zone 9 passes into line 11 and provides makeup hydrogen for hereinafter described process steps; any excess hydrogen may be recovered as a by-product. In addition, separation facilities within the dehydrogenation zone can be arranged to produce an internal hydrogen recycle stream for the dehydrogenation process. Methanol, added to etherification zone 12, reacts with isobutene to produce MTBE. After the reaction, MTBE is separated from unreacted components and withdrawn from the etherification zone by product line 13. Side reaction products, consisting primarily of oxygenate compounds, are removed from the process. Unreacted hydrocarbon components are recycled from the etherification zone to deisobutanizer 2 through line 3. Line 3 admits the recycle at a point below feed input line 1. Toward the bottom of deisobutanizer 2, a sidecut stream rich in normal butane but also containing normal butenes and some butadiene is withdrawn through line 14 and enters a hydrogenation section 15 which removes moisture from the contents of line 14. Hydrogenation section 15 also receives net hydrogen from the dehydrogenation zone through line 11. The hydrogenation zone uses used catalyst from the isomerization zone comprising platinum supported on alumina at hydrogenation conditions to saturate any butenes and butadienes. Saturated normal butanes are transferred by line 17 to a dryer section 16 which removes excess moisture from the contents of line 17. Line 18 delivers dry, saturated normal butanes from dryer zone 16 to isomerization zone 6 along with any required makeup hydrogen. Isomerization zone 6 uses the platinum catalyst at isomerization conditions to produce a mixed stream of isobutane and normal butane which is recycled back to the column through line 5 at a point above the withdrawal point of line 14. Line 5 completes the loop for isomerization which originated with line 14.

DETAILED DESCRIPTION

There are two feed materials to the subject process. One of the feed materials is a water-soluble alcohol which preferably has less than four carbon atoms per molecule. Thus, the alcohol can be chosen from methanol, ethanol, primary and secondary propanol, the various butanols, and other alcohols. However, the preferred class of alcohols are $C_4$ minus aliphatic monocyclic alcohols with methanol and then ethanol being particularly preferred. The majority of the description of the invention is presented in terms of the reaction of isobutene with methanol since these are the preferred feed materials and this is the commercially predominant reaction. However, it is not intended to thereby lessen the scope of the inventive concept. This is especially true since there have been predictions that the expected large demand for ethers as anti-knock additives will lead to the use of large amounts of ethanol produced by fermentation in etherification processes.

The second feed material is a $C_4$-$C_6$ acyclic hydrocarbon or a single carbon number mixture of isomeric hydrocarbons. The hydrocarbon feed material may therefore be substantially pure normal butane, normal pentane, or a mixture of the corresponding isomeric and normal hydrocarbons. The preferred hydrocarbon feed stream is a mixture of isobutane and normal butane such as is available from several sources in a petroleum refinery or as is available as field butanes. This variety of possible feed materials allows the production of a wide variety of ethers other than the preferred MTBE including methyl tertiary amyl ether, ethyl tertiary amyl ether and ethyl tertiary butyl ether.

The ethers are produced by the reaction of the alcohol and the isoolefin in an etherification zone. The ethers are then separated from unreacted hydrocarbons, water and unreacted alcohol to yield the ether product stream. In the case of MTBE production, the unreacted hydrocarbons include normal butenes, formed from normal butane which enters the dehydrogenation zone, and various butadienes since these compounds do not react with the alcohol. Also present is a larger amount of isobutane from the dehydrogenation zone feed stream which was not dehydrogenated. These unreacted hydrocarbons are withdrawn from the separatory facilities used to recover the ether as a separate stream. In the integrated processes to which the subject invention is directed, this hydrocarbon stream is recycled to produce more of the isoolefin by the steps of isomerization and dehydrogenation. If not removed from the process, the normal butenes and butadienes will accumulate within the process and cause the recycle stream to increase in volume. The presence of these compounds also has detrimental effects on the preferred isomerization catalyst. Other components of the hydrocarbon recycle stream include smaller amounts of various oxygenates such as the product ether, the feed alcohol and oxygen-containing reaction by-products resulting from side reactions and the presence of impurities in the feed streams. It is also not desirable to pass these oxygenates into the isomerization zone because of their effects on the preferred catalyst. It is therefore desirable to remove, alter or destroy all of these undesired compounds before the hydrocarbon recycle stream is passed into the isomerization zone.

In the process of this invention, the undesired compounds from the etherification zone recycle are returned to the fractionation column. $C_3$ and lighter compounds are withdrawn with the fractionation zone overhead and rejected by separation facilities within the dehydrogenation zone. Heavier olefinic compounds are withdrawn from the column with a sidecut of normal butanes. The sidecut stream passes through a nonselective hydrogenation zone which completely saturates the undesired compounds. The hydrogenation zone may comprise a hydrotreater which is operated at mild conditions as is done when it is desired to achieve the complete saturation of monoolefins.

The isomerization zone is a net consumer of hydrogen and therefore requires a hydrogen feed stream. This hydrogen stream, like the hydrocarbons which enter the isomerization zone via the recycle hydrocarbon stream, must be free of olefins and other undesirable chemical compounds to assure the continued good performance of the isomerization zone when using catalysts similar to the preferred isomerization catalyst. This would normally require a separate hydrogen treating unit. However, by the process of the subject invention, it is also possible to recover an olefin-containing hydrogen gas stream from the dehydrogenation zone and convert olefins from the hydrogen stream by passage through the same hydrogenation zone used to treat the hydrocarbon recycle stream. The need for a separate hydrogen treating unit within the isomerization zone is thereby eliminated and the cost and complexity of the overall process is reduced. Accordingly, integration of the hydrogen supply into the process of this invention provides a further improvement to the integrated process for producing ethers from light paraffins and alcohols.

Addition of the hydrocarbon feed material begins with its entry into the fractionation column. In this case where isobutane is the precursor of desired isoolefin, the column operates as a deisobutanizer. Isobutanes from the feed, and contributed primarily from the isomerization zone recycle, are recovered as an overhead stream from the deisobutanizer. The deisobutanizer is operated at conditions that are effective to separate the entering hydrocarbons into the net overhead stream which is rich in isobutane, a sidecut stream which is removed at a lower intermediate point and rich in normal butane and a net bottoms stream by which a relatively small amount of $C_5$-plus hydrocarbons that enter with the feed are removed. The remainder of the overhead will consist primarily of light ends and oxygenates that enter the deisobutanizer with the feed or with the recycle from the etherification zone.

The isobutane-rich overhead stream of the deisobutanizer is passed into a butane dehydrogenation zone. This zone will contain a reaction zone and associated auxiliary process equipment such as condensers and a vapor-liquid separator which receives the partially condensed reactor effluent stream. The dehydrogenation zone preferably contains at least one fractionation column. This column is designed and operated to eliminate all lighter boiling components from the net dehydrogenation zone effluent stream. These lighter boiling compounds may include some and possibly all of the propylene contained in the reactor effluent stream. The propylene may result from the dehydrogenation of propane present in the feed stream to the process or from the cracking of feed butanes. A hydrogen-rich gas stream is separated from the liquid condensed from the reactor effluent. A portion of this gas will normally be recycled and the remainder will be drawn off as a net hydrogen product gas stream. This gas stream will contain a mixture of the various olefins produced in the dehydrogenation zone at a concentration set by the separation conditions. The reaction zone preferably comprises at least one radial flow reactor in which the catalyst gradually moves downward by gravity flow to allow the continuous replacement of used catalyst with catalyst having a higher activity. It is preferred that the reactants make at least two passes through a catalyst bed within the reaction zone. A detailed description of moving bed reactors of this type may be obtained by reference to U.S. Pat. Nos. 3,647,680; 3,652,231; 3,706,536; 3,785,963; 3,825,116; 3,839,196; 3,839,197; 3,854,887 and 3,856,662.

The particular dehydrogenation conditions employed within the reaction zone may vary depending on such factors as the catalyst activity, feed carbon number and the desired conversion. The reaction zone conditions normally employed for butane dehydrogenation include a temperature of from about 500° to 700° C., a pressure of from 0.5 to about 10 atmospheres absolute and a liquid hourly space velocity of about 1 to 20. The preferred operating temperature will be within the range of from about 550° to about 660° C., and the preferred operating pressure is about 0.5 to 2 atmospheres absolute.

The preferred butane dehydrogenation catalyst is comprised of a platinum group component, a tin component and an alkali metal component with a porous inorganic carrier material. Other catalytic compositions may be used within this zone if desired.

It is preferred that the porous carrier material is an absorptive high surface area support having a surface area of about 25 to about 500 m²/g. The porous carrier material should be relatively refractory to the conditions utilized in the reaction zone and may be chosen from those carrier materials which have traditionally been utilized in dual-function hydrocarbon conversion catalysts. A porous carrier material may therefore be chosen from an activated carbon, coke or charcoal, silica or silica gel, clays and silicates including those synthetically prepared and naturally occurring which may or may not be acid-treated, as for example attapulgus clay, diatomaceous earth, kieselguhr, bauxite; refractory inorganic oxides such as alumina, titanium dioxide, zirconium dioxides, magnesia, silica-alumina, alumina-boria, titania, etc.; crystalline aluminosilicates such as naturally occurring or synthetically prepared mordenite or a combination of one or more of these materials. The preferred porous carrier material is a refractory inorganic oxide with the best results being obtained with an alumina carrier material. The crystalline aluminas, such as gamma alumina, give the best results. In general, the preferred catalysts will have a gamma alumina carrier which is in the form of spherical particles having a relatively small diameter on the order of about 1/16-inch.

The preferred alumina carrier material may be prepared in any suitable manner. For example, the alumina carrier may be prepared by adding a suitable alkaline reagent, such as ammonium hydroxide to a salt of alumina such as aluminum chloride in an amount sufficient to form an aluminum hydroxide gel which upon drying and calcining is converted to alumina. It is particularly preferred that alumina spheres are manufactured by the well-known oil drop method which comprises forming an alumina hydrosol by the techniques taught in the art, and preferably by reacting aluminum metal with hydrochloric acid, and combining the hydrosol with a suitable gelling agent. The resultant mixture is dropped into an oil bath maintained at elevated temperatures. The droplets remain in the oil bath until they set and form hydrogel spheres. The spheres are then continuously withdrawn from the oil bath and are normally subjected to specific aging treatments in oil and an ammoniacal solution to further improve their physical characteristics. The resulting pellets are then washed and dried at relatively low temperatures of about 150° to about 200° C. and calcined at a temperature of about 450° to about 700° C. for a period of about 1 to about 20 hours. See the teachings of U.S. Pat. Nos. 2,620,314; 4,250,058 and 4,273,735 for additional details on the preparation of base materials by the oil dropping method.

The preferred dehydrogenation catalyst also contains a platinum group component. Of the platinum group metals, which include palladium, rhodium, ruthenium, osmium and iridium, the use of platinum is preferred with palladium being the next preferred metal. The platinum group component may exist within the final catalyst composite as a compound such as an oxide, sulfide, halide, oxysulfide, etc., or as an elemental metal or in combination with one or more other ingredients of the catalyst. It is believed that best results are obtained when substantially all the platinum group component exists in the elemental state. The platinum group component generally comprises from about 0.01 to about 2 wt. % of the final catalytic composite, calculated on an elemental basis. It is preferred that the platinum content of the catalyst is between about 0.1 and 1.0 wt. %. The platinum group component may be incorporated into the catalytic composite in any suitable manner such as by coprecipitation or cogelation with the preferred carrier material, or by ion-exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the support with an aqueous solution of chloroplatinic or chloropalladic acid. An acid such as hydrogen chloride is generally added to the impregnation solution to aid in the distribution of the platinum group component through the carrier material.

The tin component of the preferred catalyst should constitute about 0.01 to about 5 wt. % of the final composite, calculated on an elemental basis, although substantially higher amounts of tin may be utilized in some cases. Best results are often obtained with about 0.1 to about 1 wt. % tin. It is preferred that the atomic ratio of tin to platinum is between 1:1 and about 6:1. The tin component may be incorporated into the catalytic composite in any suitable manner known to effectively disperse this component in a very uniform manner throughout the carrier material. Thus, the component may be added to the carrier by coprecipitation. A preferred method of incorporating the tin component involves coprecipitating it during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into the oil bath as previously described. The tin component may also be added through the utilization of a soluble, decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

The preferred butane dehydrogenation catalyst normally contains from 0.1 to 5.0 wt. % halogen and an alkali metal component chosen from cesium, rubidium, potassium, sodium, and lithium. The preferred alkali metal is normally chosen from lithium and potassium, with potassium being preferred for isobutane. The concentration of the alkali metal may range from 0.1 to 5.0 wt. % but is preferably between 0.5 and about 3.0 wt. % calculated on an elemental basis.

The net hydrocarbon effluent stream of the dehydrogenation zone is passed into an etherification zone. Several suitable etherification processes have been described in the available literature, with these processes being presently used to produce MTBE for petroleum chemical and gasoline additive consumption. The preferred form of the etherification zone is similar to that described in U.S. Pat. No. 4,219,678 and shown in the previously cited paper. In this instance the isobutane or other isoolefin, methanol or other feed alcohol, and a recycle stream containing recovered excess alcohol are passed into the reaction zone in which they are contacted with an acidic catalyst while maintained at etherification conditions. A wide range of materials is known to be effective as etherification catalysts for the preferred reactants including mineral acids such as sulfuric acid, boron trifluoride, phosphoric acid on kieselguhr, phosphorus-modified zeolites, heteropoly acids, and various sulfonated resins. The use of a sulfonated solid resin catalyst is preferred. These resin type catalysts include the reaction products of phenolformaldehyde resins and sulfuric acid and sulfonated polystyrene resins including those crosslinked with divinylbenzene. Further information on suitable etherification catalysts may be obtained by reference to U.S. Pat. Nos. 2,480,940; 2,922,822; and 4,270,929 and the previously cited etherification references.

A broad range of etherification conditions includes a superatmospheric pressure sufficient to maintain the reactants as a liquid phase, generally below about 200 psig, and a temperature between about 30° and 100° C. A preferred temperature range is from 50° to 100° C. The reaction rate is normally faster at higher temperatures but conversion is more complete at lower temperatures. High conversion in a moderate volume reaction zone can therefore be obtained if the initial section of the reaction zone, e.g. the first two-thirds, is maintained above 70° C. and the remainder of the reaction zone is maintained below 50° C. This may be accomplished most easily with two reactors. The ratio of feed alcohol to isoolefin should normally be maintained in the broad range of 1:1 to 2:1. With the preferred reactants, good results are achieved if the ratio of methanol to isobutene is between 1.1:1 and 1.5:1. An excess of methanol above that required to achieve satisfactory conversion at good selectivity should be avoided. Separation facilities are provided within the etherification zone for the removal of oxygenate compounds. The effluent of the etherification reaction zone is passed into an intermediate point of a secondary fractionation column designed and operated to concentrate unconverted isobutene and other saturated and unsaturated butanes present in the effluent into a net overhead stream. The net overhead stream of this column becomes the recycle hydrocarbon stream of the subject process and is passed into the deisobutanizer preferably after passage through a water wash zone to recover most of the methanol or other alcohol present in this stream. The bottoms stream of this column contains the product ether which is withdrawn as the product stream of the process. Further details on the separatory method and other aspects of the etherification zone may be obtained from the previously cited references.

Butenes and normal butane are withdrawn as a sidecut and enter an isomerization loop. Primary operations of the isomerization loop are hydrogenation and isomerization. Water poisons the preferred catalyst for the isomerization zone, therefore a drying zone, placed ahead of the isomerization zone, removes free moisture from the hydrocarbons in the sidecut stream. The drying zone may be placed ahead of the hydrogenation zone or after the dehydrogenation zone. Its location after the hydrogenation zone is preferred to remove sulfur contaminants present in the feed. The drying zone is of ordinary design such as is usually found in front of isomerization units. Two parallel chambers filled with molecular sieves are normally used so that one is on stream while the other is being regenerated.

The hydrogenation zone is designed to fully saturate all the hydrocarbons charged thereto while minimizing any cracking or polymerization of hydrocarbons passing therethrough. As a result, the hydrogenation may take on many forms, but preferably comprises a fixed bed reaction zone in which all of the entering materials are contacted with a hydrogenation catalyst at hydrogenation conditions. A broad range of hydrogenation conditions includes an LHSV (liquid hourly space velocity based at 15° C. liquid) between about 0.5 and 20, a pressure between 5 and 500 psig, and a temperature of 50° to 500° C. A preferred range of hydrogenation conditions include an LHSV of 4 to 20, a pressure of 100 to 300 psig, and a temperature of 200° to 400° C. Hydrogen is passed through the hydrogenation zone on a once through basis which also supplies makeup hydrogen for the hereinafter described hydrogenation zone.

A broad range of catalysts are commercially available for the hydrogenation zone. Suitable catalyst for this process will completely saturate mono- and polyolefinic hydrocarbons without significant cracking or polymerization activity. Such catalysts will normally comprise one or more metallic components which may be elemental metal or a metal compound. The metals are normally chosen from Groups VIII and IVA of the Periodic Table of the elements with Ni, Pd, Pt, Sn, being common metals in these catalysts. Pt is a preferred metal in these catalysts for reasons that are hereinafter explained. Based on the weight of the metal, the catalyst may contain from 0.1 to 4.0 wt. % metallic components. The metallic components of the catalyst are supported by a refractory inorganic oxide material such as one of the aluminas, silica, silica-alumina mixtures, various clays and natural or synthetic zeolitic materials. Preferably, the carrier material is alumina. Metallic components may be added to the carrier which is in the form of spheres, pellets or extrudates by impregnation, cogelation or coprecipitation. Preferably, the metallic components are impregnated by immersing an extruded particle in an aqueous solution of a metal containing compound and thereafter treating the impregnated particle by drying, calcination or other treatments.

The hydrogenation function may be served more generally by a hydrotreating zone which can take on various forms. If employed, the hydrotreating zone will preferably comprise a fixed bed reaction zone maintained at hydrotreating conditions in which all of the entering materials are contacted with a hydrotreating catalyst. A broad range of hydrotreating conditions includes an LHSV (liquid hourly space velocity based at 15° C. liquid) between about 0.5 and 20, a pressure between 100 and 500 psig, and a temperature between 50° and 500° C. A preferred range of hydrotreating conditions includes an LHSV of 4 to 20, a pressure of 100 to 300 psig, and a temperature between 200° and 400° C.

The effluent of the hydrogenation zone is passed into the isomerization zone, and provides makeup hydrogen for this zone. This effluent comprising an essentially olefin free mixture, rich in normal butane, is passed to the isomerization zone.

The isomerization zone comprises a reactor and auxiliary process equipment such as heaters, condensers, separatory vessels, etc. The isomerization zone also contains a stripping column which eliminates light ends (hydrogen, methane, ethane) from the net effluent of the isomerization zone. With the preferred catalyst, this stripping column will also remove volatile chloride compounds from the isomerization zone effluent. The core of the operation of this zone is passage of the saturated sidecut stream through a reactor maintained at butane isomerization-promoting conditions including the presence of an acidic isomerization catalyst. This is normally a relatively low pressure operation performed at a pressure of from about 50 to 600 psig and at an elevated temperature as required by the activity of the catalyst. The average reactant temperature may be as high as 500° C., but is preferably between 100° and 320° C. It is normal practice to pass the butane through the reactor in admixture with between 1 and 10 moles of hydrogen per mole of butanes to ensure vapor phase conditions and to suppress coke deposition on the catalyst. It is preferred that the butane is passed vertically through one or more fixed beds of catalyst located within the reactor at a liquid hourly space velocity between 1.0 and 5.0, but space velocities in the broad range of 0.5 to 12.0 can be employed if desired. The effluent of the isomerization reactor is normally separated into a hydrogen-rich recycle gas which is returned to the reactor and an isomerate-containing liquid stream which is passed into the deisobutanizer column. It is within the scope of the inventive concept that this liquid stream may be fractionated within the isomerization zone to allow the recycling of normal butanes and the achievement of higher conversion rates, but this is not preferred. The net hydrocarbon effluent of the isomerization zone is a mixture of isobutane and normal butane. This stream should contain at least 50 mole percent isobutane. Preferably, this stream comprises 55 to 65 mole percent isobutane. Further details on the butane isomerization step of the subject process may be obtained by referring to the references under the heading "Prior Art".

The preferred isomerization-promoting catalyst for use in the isomerization zone comprises a platinum group component and a halogen component supported by an inorganic oxide carrier. In general, the carrier material is a porous, high surface area material which is relatively refractory to the conditions utilized in the isomerization process. The carrier material may be selected from silica, alumina, titanium dioxide, chromium, or mixtures of these oxides; various naturally occurring refractory oxides in different degrees of purity, such as bauxite and bentonite clay; or a diatomaceous earth such as kieselguhr. Of the above-mentioned oxides, alumina is preferred and particularly preferred is a synthetically prepared substantially anhydrous gamma-alumina with a high degree of purity.

The preferred platinum group components are platinum and palladium or a mixture of platinum and palladium, with platinum being preferred. This, however, is not intended to exclude the other platinum group metals such as rhodium, ruthenium, osmium and iridium. A platinum group component may exist within the final catalytic composite as an oxide, a sulfide or a halide, etc., or as an elemental metal. On a weight basis, the platinum group component will comprise only a minor fraction of the total catalytic material. The preferred catalyst will therefore contain less than about 2.0 wt. % of the platinum group component, with the preferred concentration being from about 0.05 to about 1.0 wt. %. The method by which the platinum group component is made part of the catalytic composite is not controlling. It may therefore be added by coprecipitation or cogelation with the preferred carrier material or by ion-exchange or impregnation on pre-existing carrier material. The preferred method of preparing the catalyst impregnates the carrier material by contacting it with an aqueous solution of a water-soluble, decomposable compound of a platinum group metal. This may be performed by dipping the carrier material in a solution of chloroplatinic acid, ammonium chloroplatinate, bromoplatinic acid, or platinum dichloride. The utilization of a platinum chloride compound is preferred since it facilitates the incorporation of both the platinum component and at least a minor quantity of the halogen component in a single step.

There are also numerous ways in which to add the halogen component to the isomerization catalyst. The halogen component may be composited with the carrier material during the impregnation of the carrier material with the platinum group component by the utilization of a mixture of chloroplatinic acid and hydrogen chloride. Alternatively, the alumina hydrosol which is typically utilized to form the preferred alumina carrier material may contain at least a portion of the halogen. The halogen may also be added by contacting a calcined carrier material with an aqueous solution of an acid such as hydrogen chloride, hydrogen fluoride, or hydrogen bromide, etc. The halogen component may be selected from chlorine, fluorine, iodine, bromine or mixtures thereof with chlorine and fluorine being particularly preferred. The halogen component is normally referred to as a combined halogen and is typically present in an amount of from 0.01 to about 5.0 wt. % based on the dried support material.

A particularly preferred method for the production of an isomerization catalyst is presented in U.S. Pat. No. 2,999,074. The carrier material and the platinum group component are composited and the resulting material is mildly calcined. This calcination is normally carried out under carefully controlled conditions to remove physically adsorbed solvents such as water but to retain some chemically combined hydroxyl groups on the surface of the catalyst. Temperatures ranging from 350° to about 700° C. are usually satisfactory. The calcined composite is then reacted with a metal halide of the Friedel-Crafts type. Suitable metal halides include alumihum chloride, aluminum bromide, ferric chloride and zinc chloride, etc. Of these, aluminum chloride is particularly preferred.

Other recently developed isomerization catalysts including those of a bimetallic or trimetallic nature may be used in the process. An example of this is the catalytic composite comprising a platinum group component, a germanium component, and a Friedel-Crafts metal halide component shown in U.S. Pat. No., 3,649,704. In U.S. Pat. No. 3,652,697, there is disclosed a trimetallic catalyst comprising a platinum group component, a germanium component, a rhenium component and a Friedel-Crafts metal halide component.

A highly preferred catalyst for the isomerization zone comprises a platinum metal in a concentration of 0.05 to 1.0 wt. %, an alumina support which has a chloride content of 0.01 to 5.0 wt. %. This catalyst is highly preferred because it can be used fresh in the isomerization zone, wherein it provides the isomerization function. After the catalyst is spent for isomerization, i.e., has lost its isomerization function, it still retains substantial hydrogenation activity and is particularly suitable for use in the hydrogenation zone. Thus, operational costs are reduced by lowering the required inventory of platinum containing catalyst. As an added benefit, this catalyst does not give off water. Accordingly, its use in the dehydrogenation zone will not free water that would destroy the isomerization activity of the catalyst in the isomerization zone.

EXAMPLE

The following example presents the calculated operation of a process arranged in accordance with this invention for producing MTBE from a feed of mixed butanes and methanol. Major equipment for this process consists of a debutanizer column, a dehydrogenation zone, an etherification zone, dryers, a hydrogenation zone and an isomerization zone. The arrangement and interconnection of this equipment corresponds to the drawings. Additional equipment such as pumps, compressors, heat exchangers, coolers, instruments, recorders and controllers, etc. would be needed to carry out the process of this example, but have been omitted for the sake of succinctness and clarity in the presentation.

The process begins with a hydrocarbon feed entering the debutanizer column. In a typical example, feed consisting of 45% isobutane, 54% normal butane, and 1% $C_5$ and higher hydrocarbons enter the deisobutanizer at an intermediate tray level. An etherification zone recycle having 90% isobutane, 4% normal butane, 5% mixed butenes, and 2% lighter compounds such as propane and propylene enters the debutanizer at an upper tray close to the top of the column. Also entering the debutanizer at an intermediate tray level is an isomerization effluent made up of 51% isobutane, 43% normal butane, and 6% $C_5$ hydrocarbons. The location of the feed and recycle trays is chosen so that the composition of each feed stream closely matches the composition of the liquid in the trays inside the column. An overhead stream consisting of 95% isobutane, 4% normal butane, 1% mixed butenes, and traces of other light ends consisting of propane and propylene.

The overhead stream is charged to the dehydrogenation zone. A platinum type catalyst is used in the dehydrogenation zone at a temperature and pressure in the range of 600° to 700° C. and 0.5 to 4 atmospheres absolute. Contact with the catalyst produces an isobutene effluent stream having 45% isobutene and 50% isobutane along with smaller quantities of butane, butenes, and lighter compounds. In addition, an off gas stream made up of $C_3$ and lighter hydrocarbons is removed from the dehydrogenation zone which also produces a net hydrogen stream with about 88 mol % $H_2$.

The isobutene effluent enters the etherification zone where it is mixed with methanol and passes through a sulfonic resin catalyst at temperatures ranging from 40° to 100° C. and a pressure sufficient to maintain the reagents in the liquid phase. MTBE product at a purity of 99.6% is recovered from the etherification zone which also contains separation facilities from which the previously described etherification recycle stream is recovered.

Hydrocarbons, providing the unconverted material for the isomerization recycle, are withdrawn from the deisobutanizer near the bottom of the column and consist of 86% normal butanes, 5% isobutane, 3% mixed butenes including 0.1% butadiene and 6% $C_5$'s. This stream is combined with hydrogen from the dehydrogenation zone and passed to a hydrogenation zone where contact with a platinum catalyst at temperatures ranging from 150° to 250° C., and pressures of from 100 to 300 psig saturates the olefinic components thereby producing an olefin-free effluent consisting of 89% normal butane.

Olefin-free effluent enters an isomerization zone. The isomerization zone contains a platinum catalyst with the same composition as that used in the hydrogenation zone and is operated at a temperature of between 150° to 250° C. and a pressure ranging from 25 to 35 atmospheres absolute. Passing the olefin-free feed through the isomerization produces the previously described isomerization recycle which is returned to the deisobutanizer column.

A bottoms stream from the deisobutanizer removes $C_5$ and higher hydrocarbons that are present in the feed or produced in the process.

We claim as our invention:

1. A hydrocarbon conversion process which comprises the steps of:
   (a) passing a feed stream which comprises $C_4$-$C_6$ paraffins to a fractionation section;
   (b) recovering a first stream rich in isoparaffin from the fractionation section;
   (c) passing said first stream to a dehydrogenation unit and recovering a second stream rich in the isoolefin corresponding to the isoparaffin in said first stream and hydrogen containing gas;
   (d) passing at least a portion of said isoolefin from said second stream and a $C_1$-$C_5$ alcohol to an etherification zone and recovering a third stream;
   (e) separating said third stream to recover an ether rich product stream and an olefin containing fourth stream;
   (f) returning said fourth stream to said fractionation section;
   (g) recovering a fifth stream from said fractionation section, said fifth stream being rich in normal paraffins and containing olefins;
   (h) passing said fifth stream to a hydrogenation zone to saturate said olefins and recovering a sixth stream comprising saturated hydrocarbons;
   (i) passing said sixth stream to an isomerization zone and recovering a seventh stream comprising corresponding isoparaffins and normal paraffins; and
   (j) returning at least a portion of said seventh stream to said fractionation section.

2. The process of claim 1 further characterized in that said second stream passes through a separator to remove light gases prior to passing to said etherification zone.

3. The process of claim 2 further characterized in that at least a portion of the hydrogen containing gas from said second stream passes to said hydrogenation zone.

4. The process of claim 1 further characterized in that said feed comprises mixed butanes.

5. The process of claim 1 further characterized in that said isomerization zone uses a catalyst that retains a hydrogenation function after substantial deactivation of its isomerization function, and at least a portion of said catalyst is used to fulfill the catalyst requirements of said hydrogenation zone after it has undergone substantial isomerization deactivation.

6. The process of claim 5 further characterized in that said catalyst comprises a platinum group metal in a weight ratio of 0.05 to 1 wt. % on an alumina support.

7. The process of claim 1 wherein said fractionation section comprises a single column and said first stream comprises a net overhead stream from said column and said fifth stream comprises an intermediate stream from said column.

8. A hydrocarbon conversion for producing methyl tertiary butyl ether from feed materials comprising mixed butanes and butenes, and a methyl alcohol, said process comprising:

(a) passing said feed stream of said mixed butanes and butenes to a fractionation column;

(b) recovering an overhead stream consisting essentially of isobutane;

(c) passing said overhead stream to a dehydrogenation zone to convert isobutane to isobutene, and recovering a first effluent stream rich in isobutene;

(d) passing at least a portion of said first effluent and an input stream of methanol to an etherification zone and separating the effluent from said etherification zone to recover an MTBE rich product stream, and a first recycle stream comprising isobutane and olefins;

(e) passing said first recycle stream to said column;

(f) withdrawing a higher boiling fraction from said column, said higher boiling fraction being rich in normal butene and containing at least a portion of the olefins from said first recycle stream;

(g) passing said higher boiling stream to a hydrogenation zone to saturate said olefins and recovering a second effluent stream, said second effluent stream being substantially free of olefins; and (h) passing said second effluent stream to an isomerization zone to convert normal butane to isobutane and recovering a second recycle stream, rich in isobutane, and recycling at least a portion of said second recycle stream to said column.

9. The process of claim 8 further characterized in that said first effluent stream is separated to recover a hydrogen rich gas stream and at least a portion of said gas stream is passed to said hydrogenation zone to supply hydrogen.

10. The process of claim 8 further characterized in that said isomerization zone uses a catalyst that retains a hydrogenation function after substantial deactivation of its isomerization function, and at least a portion of said catalyst is used to fulfill the catalyst requirements of said hydrogenation zone after it has undergone substantial isomerization deactivation.

11. The process of claim 10 further characterized in that said catalyst comprises a platinum group metal in weight ratio of 0.05 to 1 wt. % on an alumina support.

* * * * *